(12) United States Patent
Razzano

(10) Patent No.: US 6,440,403 B1
(45) Date of Patent: *Aug. 27, 2002

(54) FINGERNAIL LACQUER EMULSION COMPOSITION

(76) Inventor: Dominick D. Razzano, 5902 NW. 40th Ter., Virginia Gardens, FL (US) 33166

( * ) Notice: Subject to any disclaimer, the term of this patent is extended or adjusted under 35 U.S.C. 154(b) by 0 days.

This patent is subject to a terminal disclaimer.

(21) Appl. No.: 09/657,694

(22) Filed: Sep. 8, 2000

(51) Int. Cl.⁷ .............................. A61K 6/00; A61K 7/00; A61K 7/04

(52) U.S. Cl. ........................................ 424/61; 424/401

(58) Field of Search .................................... 424/61, 401

(56) References Cited

U.S. PATENT DOCUMENTS

| | | | | |
|---|---|---|---|---|
| 4,166,054 A | * | 8/1979 | Meeske et al. | ......... 260/23 EP |
| 6,190,682 B1 | * | 2/2001 | Razzano | ..................... 424/401 |

* cited by examiner

Primary Examiner—Thurman K. Page
Assistant Examiner—S. Howard
(74) Attorney, Agent, or Firm—Robert M. Downey, P.A.

(57) ABSTRACT

A composition for application to fingernails and toe nails includes a binder and a pigment, the binder including volatile and non-volatile components and the pigment being present in the composition in an amount of between 25% to 35% of the total volume of the non-volatile portion of the composition, creating a physical action upon drying of a layer of the composition applied to the nails, wherein a lack of cohesive strength between the pigment and binder results in formation of random cracks in the applied layer.

8 Claims, No Drawings

FINGERNAIL LACQUER EMULSION COMPOSITION

BACKGROUND OF THE INVENTION

1. Field of the Invention

The present invention relates to a cosmetic preparation and method for applying the preparation to fingernails and toe nails.

2. Description of the Related Art

The art is crowded with various nail polish compositions and methods of applying nail art designs to fingernails. Such methods and compositions are no longer limited to a single, uniform color of nail polish applied to all of one's fingernails or toe nails. It is now commonplace to paint multi-color designs on each nail, sometimes adding sparkles, decals, and other design elements to enhance the overall appearance of the polished nails. This is usually done by airbrushing or free hand painting, both of which require a considerable degree of skill and artistic ability. For this reason, anything beyond conventional polishing of nails with a uniform color must usually be done by a professional at a nail salon.

Now that the art has gone beyond the traditional single color and French manicure, new and more unusual appearances are becoming increasingly popular. In recent years, more contemporary, and sometimes wild painted nail designs and colors have set a trend in the cosmetic industry. Among the new products which have recently been introduced to the market is a nail lacquer which leaves a crackle appearance when it dries. The crackle appearance which results using the composition of the present invention is similar to an appearance known in the furniture industry for creating an antique finish. However, the crackle lacquer used in the furniture industry is not suitable for use in the cosmetic industry, as it contains a number of toxic components which present a health hazard. In the past, others may have attempted to achieve the crackle effect in a nail polish composition, however, it is believed that such attempts have been unsuccessful due to the difficulty in producing a non-toxic crackle composition which has physical characteristics that make it suitable for application by both brushing and spraying on fingernails and toe nails. The first known success in developing a safe, non-toxic crackle lacquer which is useful and acceptable for application to fingernails and toe nails was achieved in the development of my previous nail lacquer compositions described in U.S. Pat. Nos. 5,989,575 and 5,935,590.

While several emulsion crackle fingernail polishes have reached the market, it is believed that their success has been limited due to several problems. These problems are largely due to the formulations used in the manufacture of these products. Specifically, the emulsion crackle fingernail polishes presently on the market are difficult to remove from the fingernails after 24 hours from initial application. Further, consumers complain that the emulsion crackle fingernail polishes flake or chip and, when placed in contact with soapy dishwater, the crackle lacquer softens. Also, opening and closing the bottle causes drying of the liquid crackle lacquer in the interior threads. This results in dry particles falling inside the bottle and contaminating the liquid contents.

In view of the strong demand for unique and attractive nail polish products in the industry, and particularly crackle fingernail polishes, the present invention attempts to improve the previously known emulsion crackle nail polishes which are presently on the market. More particularly, it is an object of the present invention to eliminate the problems associated with existing emulsion crackle nail polishes which are presently on the market.

SUMMARY OF THE INVENTION

The present invention is directed to a cosmetic preparation and a method of applying the cosmetic preparation to fingernails and toe nails. The cosmetic preparation includes a crackle composition for application to nails which have one or more coats of previously applied conventional colored nail polish thereon. This crackle composition includes a pigment and a binder provided in a ratio to create a physical action upon drying of a layer applied to the nails, wherein a lack of cohesive strength between the pigment and the binder results in shrinking of the applied layer to form cracks therein. The previously applied underlying colored nail polish is thus visible through the cracks formed in the overlying layer of the crackle composition which is of a different color.

Contributing to the crackle formation is a softer base upon which the crackle composition is applied. This results in a harder film of the crackle composition when dried. The different in contraction between the dried base coat and the crackle coat produces additional cracking on the top coat. In a preferred embodiment, the solvents or volatiles in the crackle composition (resin portion) are 50% water, 2% surfactants, and 3% coalescent. In a preferred embodiment, the crackle composition has a pigment volume concentration (PVC) of approximately 30% (±5%). The resin content is a phenyl ethylene acrylic copolymer emulsion with a glass transition temperature of 44° C.±10° C. The coalescent is dipropylene glycol methyl ether, or equivalents thereto. The crackle coat composition can be either brushed or sprayed on the nails to provide a uniform layer thereon. During air drying, which requires approximately five to ten minutes, cracking of the applied crackle coat occurs and two colors become visible; the color of the crackle coat and the color of the conventional fingernail polish which appears through the cracks of the crackle coat layer.

To obtain a high gloss over the crackle coat, a conventional clear gloss layer can be brushed or sprayed over the crackle coat layer after the crackle coat layer has completely dried. For the highest gloss, two coats of clear gloss lacquer can be applied.

DETAILED DESCRIPTION OF THE PREFERRED EMBODIMENT

The cosmetic preparation of the present invention provides a novel and distinct visual appearance on polished fingernails. In contrast to the one solid color appearance produced by conventional fingernail polish products, the cosmetic preparation of the present invention produces two colors with a randomly created crackle design. More specifically, the top crackle coat appears as one color while a different color of the underlying coat of conventional nail polish is visible through the cracks formed in the top crackle coat.

The cosmetic preparation of the present invention is useful in combination with virtually any commercially available fingernail polish. The cosmetic preparation includes two separate compositions which are applied independently of the other by either brushing or spraying. Specifically, the cosmetic preparation includes a clear coat base composition which is applied to the surface of any dry colored fingernail polish which has been previously painted on the fingernails or toe nails. The clear coat base composition is applied in a uniform layer by either brushing or spraying over the surface of the previously polished nails, and allowed to dry for three to ten minutes at ambient temperature.

The cosmetic preparation further includes a crackle coat composition which comprises non-toxic ingredients, including a binder portion and a pigment portion. The binder portion includes volatile and non-volatile components, and more specifically, select resins. The pigment portion includes one or more color pigments and a pigment extender. As a practical matter, the pigments used in nail polish must conform to appropriate national legislation. The color pigments used in the composition of the present invention are all certified by the Food & Drug Administration (FDA). The crackle coat composition is applied to the exposed, dry surface of the base coat by either brushing or spraying. The applied layer of the crackle coat should be uniform across the entire upper side of the nails. During drying for a period of five to ten minutes at ambient temperature, the applied layer of crackle coat forms random cracks in the applied layer, thereby exposing the color of the underlying conventional nail polish. This phenomenon of cracking of the crackle coat layer is a physical reaction which results from over pigmentation plus using a specific water borne resin with a glass transition temperature of 44° C.±10° C. More specifically, the crackle coat composition includes a pigment and a binder which are provided in a ration that creates a lack of cohesive strength between the pigment and binder. This results in shrinking of the applied layer of the crackle coat composition when drying, thereby creating the desired cracks. The amount of pigment in the composition, or pigment volume concentration (PVC), is expressed in terms of the percentage of the volume of pigment in relation to the total volume of the non-volatile portion of the composition. Satisfactory results have been achieved with a pigment volume concentration ranging between 25% and 35%.

In many instances, the clear coat base composition can be omitted, depending upon the surface quality and chemical composition of the particular fingernail polish which has been previously applied to the nails. However, to ensure a uniform foundation for subsequent coatings, application of the clear coat base composition is generally recommended prior to applying the crackle coat composition. The clear base coat further prevents bleeding or migration of the conventional nail polish through to the subsequently applied crackle coat composition, thereby serving as a barrier.

The compositions of the present invention include an emulsion, a resin, one or more FDA certified pigments, and pigment extenders. The following are examples of each of these components.

Volatile Solvents and Coalescents
Propylene glycol methyl ether acetate
Dipropylene glycol methyl ether (glycol ether solvent)
Water Resins Phenyl ethylene-acrylic copolymer emulsion with a glass transition temperature of 44° C.±10° C.

Pigment

FD&C colors (FDA certified pigments)

Pigment Extenders

Magnesium silicate (Vantac 6H)
Silicone dioxide (Amorphous silica)
Aluminum stearate
Calcium carbonate
Barium sulfate
Aluminum silicate
Calcium silicate
Calcium sulfate The following examples are illustrative of compositions of the cosmetic preparation of the present invention.

EXAMPLE 1

A clear coat base composition, comprising a petroleum naphtha, n-butyl acetate, ¼ sec nitrocellulose, a plasticizer, propylene glycol methyl ether acetate, and ethyl acetate was prepared with the following ingredients in the indicated concentrations:

| Ingredient | Pounds | Gallons | % Non Volatile | Supplier |
|---|---|---|---|---|
| Petroleum naphtha (VMP) | 105.72 | 17.34 | 0% | Shell Chemical Co. Houston, TX |
| n-butyl acetate | 135.77 | 18.60 | 0% | Eastman Chemical Kingsport, TN |
| ¼ sec nitro-cellulose | 93.00 | 8.94 | 70% | Hercules Wilmington, DE |
| Isopropyl alcohol | 21.50 | 3.30 | 0% | Eastman Chemical Kingsport, TN |
| 2-ethylhexyl diphenyl phosphate (Santicizer 141) | 84.90 | 9.25 | 100% | Monsanto Springfield, MA |
| #15 Castor Oil | 3.00 | 0.35 | 100% | Cas Chemical Bayonne, NJ |
| Propylene glycol methyl ether acetate (P.M.A.) | 25.80 | 3.11 | 0% | Dow Chemical Midland, MI |
| Ethyl acetate | 18.77 | 2.53 | 0% | Eastman Chemical Kingsport, TN |
| TOTAL | 487.96 | 63.42 | | |

Description: A batch (487.96) of the clear coat base composition was prepared in accordance with the following procedure: The ingredients, as listed above, are added, one at a time, in the order presented, beginning with petroleum naphtha. After adding each ingredient, the mixture is stirred until the added ingredient is completely blended with the previously ingredients. This process of adding and stirring in each ingredient is continued until all ingredients have been completely blended in a homogenous mixture. The resultant mixture is then thinned using butyl acetate and a brushing viscosity of 35 secs. No. 2 Zahn Cup is achieved. *If a colored line of base coats be desired, instead of applying a clear base coat over previous painted fingernails, the following formula is offered:

EXAMPLE 2

White Base Coat

| | Lbs. | Gals. | Remarks |
|---|---|---|---|
| Example 1 | 487.96 | 63.42 | The titanium dioxide is Cowles dispersed in 55 lbs. of |
| Titanium oxide | 28.00 | 0.82 | Example 1 and any other |
| | 515.96 | 64.24 | color can be substituted |
| Viscosity = 60" ± 10" | | | for the titanium dioxide. |
| #2 Zahn cup | | | However, since specific gravity |
| Wt./Gal. = 8.03 lbs. | | | and oil absorption values vary for the different colors, adjustments in the quantities used must be performed |

A brushed film of the above directly on the fingernail is allowed to air dry 5–7 minutes. A thin wet film of the crackle is applied over this base. Crackling of this coat should appear in 2–5 minutes.

A crackle composition in Example 3 in accordance with a preferred embodiment of the present invention, comprises a two step operation. The first is the addition of formula ingredients in the order listed up to the pigment. Secondly, the pigment DC Red #7 calcium lake is weighed apart with an indicated weights of the clear portion and dispersed with a "Cowles Disperser" to a grind of #6–#7 on the "North Grind Gauge" (see page 12).

NOTE: All finished batches (Examples 1, 2, 3) are put through a 325 mesh wire strainer just before filling off in bottles.

EXAMPLE 3

A Colored (Red) Crackle Coat

(Brushed Over 2 Base Coat)

| Ingredient | Lbs. | Gals. | Trade Name | Supplier |
|---|---|---|---|---|
| Phenyl ethylene acrylic copolymer emulsion | 122.6 | 13.69 | Joncryl 537 | S. C. Johnson Polymer |
| Magnesium silicate | 36.6 | 1.62 | Vantac | R. T. Vanderbilt |
| Hectorite Clay | 1.0 | 0.07 | Bentone EW | Rheox, Inc. |
| Amorphous silicon dioxide | 2.1 | 0.13 | OK412 | Degusa AG |
| Pre-Mix | | | | |
| Propylene glycol methyl ether | 5.0 | 0.65 | PM | Dow Chemical |
| Dipropylene glycol methyl ether | 4.4 | 0.55 | DPM | Dow Chemical |
| Distilled Water | 10.0 | 1.20 | | |
| When the above is all well mixed, check viscosity. | | | | |
| Water* | 20.0 | 2.40 | | |
| | 201.70 | 19.73 | | |
| D&C Red #7** | 6.00 | 0.28 | | |
| Calcium Lake | 207.70 | 20.14 | | |

*Hold for viscosity check
**Color example: To disperse the red color, a Cowles to #6–#7 Grind can be used using the following formula:
  8.0 lbs. of colorless part above
  6.0 lbs. D&C #7 Red Calcium Lake
  2.0 lbs. Distilled Water 16.0 lbs.
Note: Add 4 fl. oz. BYK 022 (Supplier - Chemie) to finished batch if micro foam should persist after overnight standing
Physical Constants: Viscosity = 45" ± 10" (30° C.)
Wt./Gal. = 10.4
% NVM = 49 ± 3
PVC = 30–40
T° g = 44° C. ± 10° C.

Transparent Coat (Third and Final Coats)

A transparent top coat provides a means to protect the crackle coat against possible abrasions during one's daily routine. The top coat also regulates the desired degree of gloss. In a preferred embodiment, the top coat consists of one or more coats of any commercial clear gloss transparent fingernail polish. Best results require waiting at least 10–20 minutes after application of the crackle coat before application of the top coat, so that the crackle coat has sufficient time to dry.

The specific mixing equipment used during the manufacturing of the composition may vary and it is recognized by those skilled in the art that the specific order and amount of each of the ingredients may change depending upon the particular mixing equipment used. To this end, the composition may have to be fine tuned to accommodate the specific manufacturing equipment, as well as the commercial production standards.

While the instant invention has been described in accordance with preferred embodiments thereof, it is recognized that departures from the instant disclosure may be made within the spirit and scope of the present invention, and such departures shall not be limited except as set forth in the following claims as interpreted under the doctrine of equivalents.

What is claimed is:

1. A lacquer emulsion composition for application to fingernails and toenails comprising:
   a non-toxic binder portion comprising volatile and non-volatile components;
   a non-toxic pigment portion; and
   said pigment portion being present in the composition in a volume of concentration ranging between 25% and 35% of the total volume of a non-volatile portion of the composition and said volume of concentration of said pigment portion causing the formation of random cracks in said composition upon drying of an applied layer of said composition.

2. A lacquer emulsion composition as recited in claim 1 wherein said binder portion comprises:
   phenyl polyethylene—acrylic copolymer emulsion with a glass transition temperature of 44° C. ±10 °C.; and
   acrylic copolymer emulsion.

3. A lacquer emulsion composition as recited in claim 2 wherein said pigment portion includes:
   at least one FDA certified color; and
   a pigment extender.

4. A lacquer emulsion composition as recited in claim 1 wherein said non-volatile components of said binder comprise resins selected from the group consisting of
   polyethylene-acrylic and copolymer emulsion (of a glass transition temperature of =44° C.)±10° C.;
   vinylidene chloride copolymer emulsion;
   acrylic ester copolymer emulsion;
   cellulose acetate butyrate emulsion;
   nitrocellulose emulsion; and
   ethyl cellulose emulsion.

5. The lacquer emulsion composition as recited in claim 1 wherein said volatile components of said binder portion comprises solvents selected from a group consisting of:
   propylene glycol methyl ether acetate;
   water; and
   dipropylene glycol methyl ether.

6. The lacquer emulsion composition as recited in claim 1 wherein said pigment portion comprises at least one pigment extender selected from the group consisting of:
   magnesium silicate;
   silicon dioxide;
   aluminum stearate;
   calcium carbonate;
   barium sulfate;
   aluminum silicate;
   calcium silicate; and
   calcium sulfate.

7. A method of decorating fingernails and toe nails comprising the steps of:

provide a lacquer emulsion composition comprising:

a non-toxic binder portion comprising volatile and non-volatile components;

a non-toxic pigment portion;

said pigment portion being present in the lacquer composition in a volume of concentration ranging between 25% and 35% of the total volume of a non-volatile portion of the lacquer composition;

applying a layer of said lacquer composition to a surface on a nail;

drying said applied layer; and forming random cracks in said applied layer to visibly expose said surface through said randomly formed cracks.

8. A method of decorating fingernails and toe nails comprising the steps of:

providing a lacquer emulsion composition comprising:

a non-toxic binder portion comprising volatile and non-volatile components;

a non-toxic pigment portion;

applying a layer of said lacquer emulsion composition to a surface on a nail;

drying said applied layer; and causing random cracks to form in said applied layer by providing said pigment portion in a volume of concentration ranging between 25% and 35% of the total volume of a non-volatile portion of the composition, thereby visibly exposing said surface through said cracks in said applied layer.

* * * * *